United States Patent
Behnam

(10) Patent No.: US 11,311,483 B2
(45) Date of Patent: Apr. 26, 2022

(54) CURCUMIN SOLUBILISATE

(71) Applicant: AQUANOVA AG, Darmstadt (DE)

(72) Inventor: Dariush Behnam, Rossdorf (DE)

(73) Assignee: AQUANOVA AG, Darmstadt (DE)

( * ) Notice: Subject to any disclaimer, the term of this patent is extended or adjusted under 35 U.S.C. 154(b) by 0 days.

(21) Appl. No.: 14/653,560

(22) PCT Filed: May 15, 2013

(86) PCT No.: PCT/EP2013/001427
§ 371 (c)(1),
(2) Date: Jun. 18, 2015

(87) PCT Pub. No.: WO2014/094921
PCT Pub. Date: Jun. 26, 2014

(65) Prior Publication Data
US 2015/0342881 A1   Dec. 3, 2015
US 2016/0128939 A9   May 12, 2016

(30) Foreign Application Priority Data

Dec. 19, 2012   (DE) .................... 20 2012 012 130.8

(51) Int. Cl.

| | |
|---|---|
| A61K 9/107 | (2006.01) |
| A61K 31/12 | (2006.01) |
| A61K 9/48 | (2006.01) |
| A23L 2/56 | (2006.01) |
| A61K 36/9066 | (2006.01) |
| A23L 33/10 | (2016.01) |
| A23L 2/52 | (2006.01) |
| A23L 5/43 | (2016.01) |
| A23L 27/10 | (2016.01) |
| A61K 31/121 | (2006.01) |
| A23L 33/105 | (2016.01) |
| A61K 47/26 | (2006.01) |
| A23L 2/39 | (2006.01) |
| A23P 10/30 | (2016.01) |
| A23D 7/005 | (2006.01) |

(52) U.S. Cl.
CPC .......... *A61K 9/1075* (2013.01); *A23D 7/0053* (2013.01); *A23L 2/39* (2013.01); *A23L 2/52* (2013.01); *A23L 2/56* (2013.01); *A23L 5/43* (2016.08); *A23L 27/10* (2016.08); *A23L 33/10* (2016.08); *A23L 33/105* (2016.08); *A23P 10/30* (2016.08); *A61K 9/4808* (2013.01); *A61K 9/4858* (2013.01); *A61K 31/12* (2013.01); *A61K 31/121* (2013.01); *A61K 36/9066* (2013.01); *A61K 47/26* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2002/0025360 | A1* | 2/2002 | Yang | A23G 3/362 426/72 |
| 2003/0105157 | A1* | 6/2003 | Behnam | A23D 7/011 514/458 |
| 2006/0275516 | A1* | 12/2006 | Ram | A61K 31/12 424/756 |
| 2007/0148309 | A1* | 6/2007 | Behnam | A23L 1/3002 426/601 |
| 2008/0220102 | A1* | 9/2008 | Behnam | A23L 33/105 424/730 |
| 2011/0293678 | A1 | 12/2011 | Behnam | |
| 2011/0294900 | A1* | 12/2011 | Kohli | A61K 31/12 514/679 |
| 2012/0010297 | A1 | 1/2012 | Chaniyilparampu et al. | |
| 2012/0052095 | A1 | 3/2012 | Chaniyilparampu et al. | |

FOREIGN PATENT DOCUMENTS

| | | |
|---|---|---|
| CN | 1682701 A | 10/2005 |
| CN | 101543486 A | 9/2009 |
| CN | 102361552 A | 2/2012 |
| CN | 102361552 A | 9/2012 |
| DE | 202004003241 U1 | 7/2005 |
| DE | 202009016292 U1 | 5/2011 |
| EP | 2192160 A1 | 6/2010 |
| JP | 2004531530 A | 10/2004 |
| JP | 2004534853 A | 11/2004 |
| JP | 2005185237 A * | 7/2005 |
| JP | 2005185237 A | 7/2005 |
| JP | 2005328839 A | 12/2005 |

(Continued)

OTHER PUBLICATIONS

Kurien et al. Assay and Drug Development Technologies 2007 5(4):567-576.*
Cui et al. International Journal of Pharmaceutics 2009 371:148-155.*
Becher Dictionary of Colloid and Surface Science New York:Marcel Dekker, Inc., 1990. Micelle entry.*
Liu et al. Chemical and Pharmaceutical Bulletin 2011 59(2):172-178.*
Abd El-Galeel Solubility and Stability of Natural Food Colorants in Microemulsions 2002.*
Benet et al. Toxicologic Pathology 1995 23:115-123 (Year: 1995).*
Sun et al. Journal of Cosmetic Science 2005 56:253-265 (Year: 2005).*

(Continued)

*Primary Examiner* — Robert A Wax
*Assistant Examiner* — Caralynne E Helm
(74) *Attorney, Agent, or Firm* — Fish & Richardson P.C.

(57) ABSTRACT

A solubilisate consisting of curcumin in a quantity of less than or equal to 10% by weight, preferably less than or equal to 7.5% by weight, particularly preferably 6% by weight, and at least one emulsifier having an HLB value in the range between 13 and 18, in particular polysorbate 80 or polysorbate 20 or a mixture of polysorbate 20 and polysorbate 80, wherein the average diameter of the micelles loaded with curcumin is between 5 nm and 40 nm, preferably between 6 nm and 20 nm, particularly preferably between 7 nm and 10 nm.

6 Claims, 1 Drawing Sheet

(56) References Cited

FOREIGN PATENT DOCUMENTS

| JP | 4206923 B2 | 1/2009 |
|---|---|---|
| JP | 2010265223 A | 11/2010 |
| JP | 2012508794 A | 4/2012 |
| WO | 9803170 | 1/1998 |
| WO | 2008101344 A1 | 8/2008 |
| WO | 2010070665 A2 | 6/2010 |
| WO | 2010106191 A1 | 9/2010 |
| WO | 2010109482 A2 | 9/2010 |
| WO | 2012116272 A2 | 8/2012 |
| WO | 2012122279 A1 | 9/2012 |

OTHER PUBLICATIONS

Liu et al. Chemical and Pharmaceutical Bulletin 2001 59(2):172-178 (Year: 2001).*
Holman et al. Chemistry. Thomas Nelson and Sons Ltd:London 2001 p. 15-16 (Year: 2001).*
Moretton et al. Journal of the Royal Society Interface 2012 9:487-502 (Year: 2012).*
www.grc.nasa.gov/www/k-12/airplane/state.html 2 pages (Year: 2011).*
Walter et al. Biochimica et Biophysica Acta 2000 1508:20-33 (Year: 2000).*
Yan et al. Biological and Pharmaceutical Bulletin 2011 34(8):1179-1186 (Year: 2011).*
"Office Action" issued in counterpart Chinese Patent Application No. 201380067238.X, dated Mar. 18, 2016, Published in: CN.
"Office Action" issued in counterpart Japanese Patent Application No. 2015-548242, dated May 16, 2016, Published in: JP.
Hui Ju et al., "Preparation and characterization of curcumin solid lipid nanoparticles", "Drug Evaluation Research", Dec. 31, 2010, vol. 33, No. 6, Published in: CN.
Jack Appiah Ofori et al., "Novel Technologies for the Production of Functional Foods", "Bio-Nanotechnology: A Revolution in Foods, Biomedical and Health Sciences", Publisher: John Wiley & Sons, Ltd., Published in: US.
"German Ssearch Report" issued in counterpart German Application No. 202012012130.8, dated Aug. 26, 2013, Published in: DE.
Nano-sized natural food ingredients—Emerging considerations from the Leatherhead food Search workshops and beyond, http://www.nutrafoods.eu/Detail.aspx?id=70, "NUTRAfoods International Journal on Nutraceuticals, Functional Foods and Novel Foods from Research to Industrial Applications", Aug. 22, 2013, vol. 10, No. 1, Published in: EU.
"NovaSOL Curcumin Natural health in crystal clear solutions", www.aquanova.de, Publisher: Aquanova AG, Published in: DE.
Michael Goetz, "International Application No. PCT/EP2013/001427 International Preliminary Report on Patentability", dated Feb. 11, 2015, Publisher: ISA/EP, Published in: EP.
"International Patent Application No. PCT/EP2013/001427 International Search Report and Written Opinion", dated Dec. 18, 2013, Publisher: ISA / EP, Published in: EP.
Aqua Nova, "Produkt-Datenblatt Curcumin Wasser-und fettloesliches 6 %iges Circumin-Solubiliasat", "NovaSOL Curcumin", Jan. 1, 2009, pp. 1-2, vol. 06.11.06, No. XP055092340, Publisher: URL: http://aquanova.de/media/public/pdb/PDB_EW0124_5_NovaSOL Curcumin.pdf, Published in: DE.
Ma, et al., "High-performance liquid chromatography analysis of curcumin in rat plasma: application to pharmacokinetics of polymeric micellar formulation of curcumin", "Biomedical Chromatography", Mar. 5, 2007, pp. 546-552, vol. 21, No. XP055154365, Publisher: Wiley InterScience.
"English Translation of the International Preliminary Report on Patentability, issued in International Application PCT/EP2013/001427".
"Office Action" issued in counterpart Japanese Patent Application No. 2015-548242, dated Sep. 29, 2016, Published in: JP.
"Office Action" issued in counterpart Russian Patent Application No. 2015129577, dated Aug. 2, 2016, Published in: RU.
"Office Action" issued in co-pending Japanese patent application No. 2015-528242, dated Feb. 13, 2017, Published in: JP.
"Chinese Office Action", Chinese Patent Application No. 201380067238. X, dated Jun. 14, 2017, 20 pp.
Schiborr et al., 'The oral bioavailability of curcumin from micronized powder and liquid micelles is significantly increased in healthy humans and differs between sexes', 2014. Molecular Nutrition & Food Research published by Wiley-VCH Verlag GmbH & Co. KGaA, Weinheim, pp. 516-527, vol. 58.
Prof. Khayyal, 'Progress Report III on the chronic anti-inflammatory effect of Curcumin (native and solubilized forms) given alone or in combination with Boswellia or Xanthohumol', May 2017; Department of Pharmacology; Faculty of Pharmacy; Cairo University, pp. 1-8.
Kocher et al., 'The oral bioavailability of curcuminoids in healthy humans is markedly enhanced by micellar solubilisation but not further improved by simultaneous ingestion of sesamin, ferulic acid, naringenin and xanthohumol', Oct. 14, 2014, Elsevier; Journal of Functional Foods 14, pp. 183-191.
Khayyal et al., Poster; 'A new solubilized formulation of Curcumin, Boswelliaand Xanthohumolextract markedly enhances anti-inflammatory activity' 2018.
C.P. Khare, 'Indian Medicinal Plants', © Springer Science+BusinessMedia, LLC., pp. 1-836, 2007.
Bisht et al., "Polymeric nanoparticle-encapsulated curcumin ("nanocurcumin"): a novel strategy for human cancer therapy", Apr. 17, 2007, Journal of Nanobiotechnology, pp. 1-18, 2007, 5:3, http://www.jnanobiotechnology.com/content/5/1/3.
Anand et al., "Design of curcumin-loaded PLGA nanoparticles formulation with enhanced cellular uptake, and increased bioactivity in vitro and superior bioavailability in vivo", Biochemical Pharmacology 79 (2010), pp. 330-338, www.elsevier.com/locate/biochempharm.
Garidel and Hildebrand, "Thermodynamic properties of association colloids," J. Therm. Anal. Cal., 2005, 82:483-489.

* cited by examiner

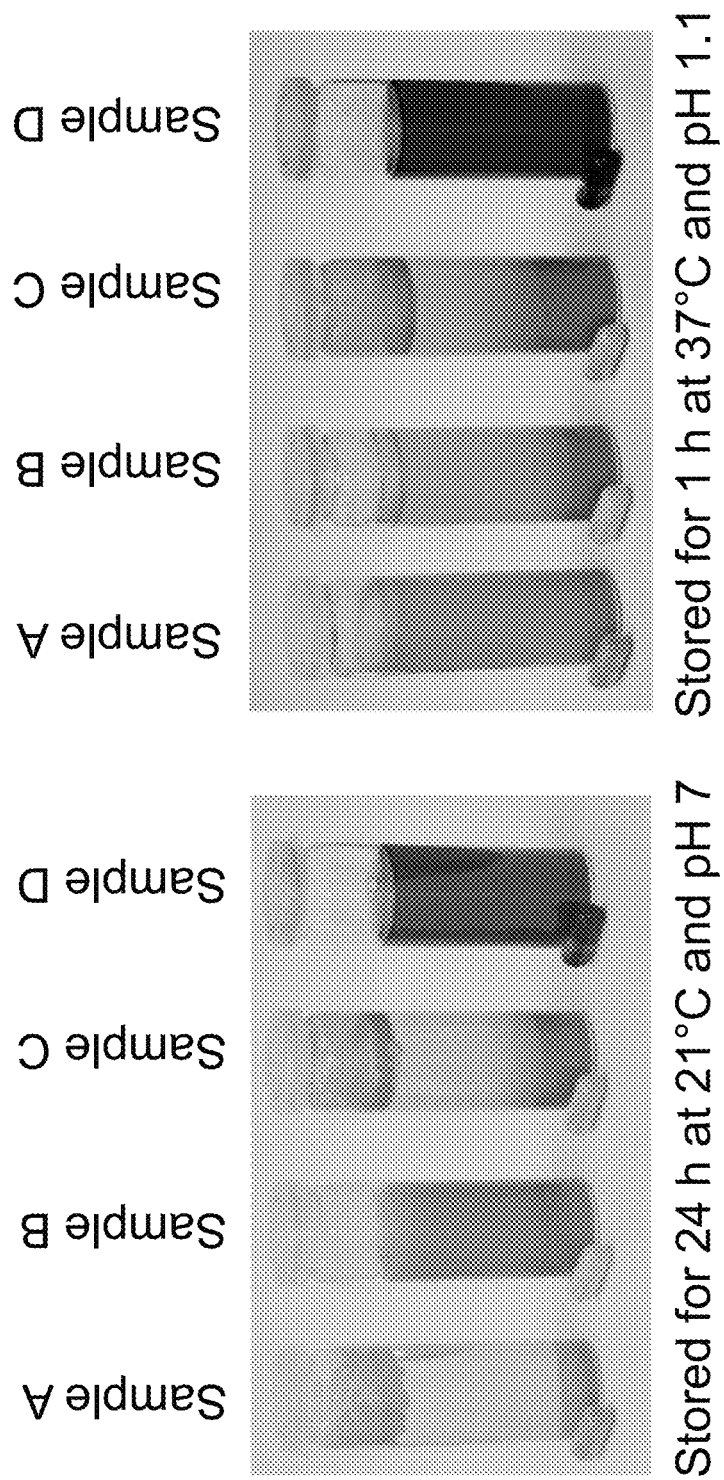

CURCUMIN SOLUBILISATE

CROSS-REFERENCE TO RELATED APPLICATIONS

This application is a National Stage application under 35 U.S.C. § 371 of International Application No. PCT/EP2013/001427, filed on May 15, 2013, which claims benefit of German Application No. 20 2012 012 130.8, filed on Dec. 19, 2012, the contents of which are hereby incorporated by reference in their entirety.

BACKGROUND

Curcumin is a turmeric extract that has been well known around the world for 5 decades, through the publication of numerous study results, as a spice, a food coloring (E100), as well as a medicament in traditional medicine, and in recent decades in mainstream medicine, as an effective active substance in immunology, osteogenesis, angiogenesis, neurogenesis, and carcinogenesis.

Curcumin is offered in numerous end products (nutritional supplements), such as in capsules or in liquid cloudy beverages, in its native form (powder), or combined with auxiliary substances such as oil, glycerin, ethanol, phospholipids or lecithin, cyclodextrin, gum arabic, gelatins, pectins, sugar esters of fatty acids, or saponins. However, it is problematic that these formulations are not transparent, do not result in an aqueous clear solution, and have extremely low absorption, i.e., bioavailability.

The use of further components in addition to curcumin for producing carrier systems, for example emulsions or liposomes, is known for increasing the bioavailability. Whereas in emulsions the curcumin is dissolved in a lipophilic phase and stabilized in droplet form in an aqueous environment, in liposomes the curcumin may be held in a phospholipid layer. Although the bioavailability may be increased by up to 50%, these types of formulations such as liposomes are extremely unstable mechanically, and also are not resistant to the environment in the stomach.

Curcumin has attracted special attention in mainstream medicine, in particular in conjunction with neurogenesis (Alzheimer's disease, among others) and carcinogenesis (cancer). To allow preventative action to be taken against these primarily age-related common ailments, which are beginning to have alarming economic impacts, it is an object of the invention to optimize the absorption, i.e., bioavailability, of curcumin by means of an appropriate, suitable formulation. It is a further object of the invention to achieve a stable, homogeneous fine distribution of curcumin in the corresponding end products, such as dietary and nutritional supplements.

SUMMARY

The invention provides a micellar curcumin formulation, on the basis of which bioavailability that is at least 230 times higher in comparison to native curcumin has been established in a human study. The invention provides a solubilisate consisting of curcumin in a quantity of less than or equal to 10% by weight, preferably less than or equal to 7.5% by weight, particularly preferably 6% by weight, and at least one emulsifier having an HLB value in the range between 13 and 18, in particular polysorbate 80 or polysorbate 20 or a mixture of polysorbate 20 and polysorbate 80, wherein the average diameter of the micelles loaded with curcumin is between 5 nm and 40 nm, preferably between 6 nm and 20 nm, particularly preferably between 7 nm and 10 nm.

BRIEF DESCRIPTION OF DRAWINGS

FIG. 1 shows photographs of curcumin formulation samples.

DETAILED DESCRIPTION

High loading of the micelles with curcumin may thus be advantageously achieved without the micelles bursting and the curcumin being released as sediment upon dilution with water.

The transparent, completely stable water-soluble curcumin formulation according to the invention, without the above-mentioned auxiliary substances such as in soft and hard gelatin capsules, has stable transparency and also greatly improved bioavailability, independently of pH, in gelatin-free capsules (hard and/or soft) and in beverages or liquid, water-based end products. Products having such transparency and water solubility, but also in particular such a high bioavailability of the curcumin formulation, are in urgent demand by the relevant industry for innovative products as a capsule filling and as transparent curcumin beverages. To the knowledge of the inventor, a curcumin formulation which meets these requirements has not existed heretofore.

The particularly small size of the micelles in the solubilisate according to the invention results in a clear, permanently transparent product. The narrow particle size distribution also contributes to this end, since the diameter distribution of the micelles ranges only from approximately 4 nm to approximately 30 nm.

The particle size distribution of the micelles was measured according to the principle of dynamic light scattering in a 180° backscattering system, using laser light having a wavelength of 780 nm. Due to the small particle sizes, the formation of a liquid which is clear, in particular for perception by the human eye, is advantageously achieved. The clarity of the solubilisate may also be represented by its lowturbidity.

To this end, the following working hypothesis is used: The clearer an aqueous dilution of a solubilisate or some other formulation of curcumin, the better its solubilization. The better the solubilization, the better the bioavailability.

The solubilisate according to the invention is further characterized in that the total curcuminoid concentration in human blood plasma, measured one hour after oral administration of 500 mg curcumin in the form of the solubilisate, is approximately 500 ng curcuminoid per ml plasma±100 ng curcuminoid per ml plasma. In contrast, when native curcumin is taken orally in powdered form, only approximately 1.3 ng curcuminoid per ml plasma is achieved after one hour.

The human study on which these values are based was conducted on 24 healthy persons between 19 and 29 years of age, who received a single oral dose of 500 mg native curcumin or curcumin in the form of the solubilisate according to the invention. Blood samples were withdrawn at various times over a period of 24 hours after the curcumin was taken. To minimize the possible concurrent influence of digested food, the test subjects were served standardized meals. One hour after taking the curcumin in native form, less than 1 nmol/l plasma was measured; 8 hours after administration, 2.4 nmol/l was measured; and 24 hours after administration, 2.4 nmol/l was measured. In contrast, for curcumin from the solubilisate according to the invention, one hour after administration, 1,964 nmol/l was measured in the blood plasma; 8 hours after administration, 307.1 nmol/l was measured; and 24 hours after administration, 67.7 nmol/l was measured. A solubilisate containing 66.5% by weight curcumin was used (the commercial product "6% NovaSOL Curcumin" of the applicant). Thus, the curcumin concentration in the blood plasma showed increases by a factor between 36 and 2800 as a result of the formulation as solubilisate according to the invention, compared to native curcumin.

The area under the curve of the total curcumin concentration in the blood plasma (area under the total curcumin plasma concentration-time curve (AUC)), measured over a period of 24 hours, was 42.6 nmol h/L for administration of native curcumin, and 9,821.4 nmol h/L for administration of the solubilisate according to the invention. In somewhat generalized terms, it may be said that the plasma AUC of the curcumin solubilisate according to the invention over 24 hours is in the range of approximately 9,500 to approximately 10,000 nmol h/L.

Accordingly, the bioavailability of the 66.5% curcumin solubilisate is much better than that of the native form. Viewed as the plasma AUC over 24 hours, the bioavailability as a result of the formulation according to the invention of the solubilisate is approximately 230 times higher.

This may be deduced from the particularly low turbidity of the solubilisate, which may be understood as a type of indicator of the bioavailability. The turbidity of the solubilisate according to the invention is less than 30 FNU, preferably less than 20 FNU, and particularly preferably is in the range between 0.5 FNU and 2 FNU, determined by scattered light measurement with infrared light according to the requirements of the ISO 7027 standard at a dilution of the solubilisate in water in a ratio of 1:1000.

The solubilisate according to the invention maintains this low turbidity after 24 hours storage at 21° C. and pH 7, as well as after 1 hour storage at 37° C. and pH 1.1, i.e., under storage conditions on the one hand at room temperature in aqueous dilution, and on the other hand, during passage through the stomach. Therefore, according to the present knowledge of the inventor, the curcumin in the solubilisate according to the invention is still present in the form of the stable, very small micelles even after passage through the stomach, and may therefore by absorbed particularly well in the further digestive tract.

For experimentally determining the turbidity, the turbidity measuring devices are calibrated with a standard suspension. Thus, the indication is provided not in the form of the measured light intensity, but, rather, as the concentration of the calibration suspension. During the measurement of any given suspension, the indication thus signifies that the liquid in question has caused the same light scattering as the standard suspension of the indicated concentration. The internationally established turbidity standard is formazin. The most commonly used units are "FNU" (formazin nephelometric units). This is the unit that is used, for example, in water treatment for the measurement at 90° according to the requirements of the ISO 7072 standard. The turbidity of the solubilisate according to the invention is less than 30 FNU, preferably less than 20 FNU, and is particularly preferably in the range between 0.5 FNU and 2 FNU, determined by scattered light measurement with infrared light according to the requirements of the ISO 7027 standard at a dilution of the solubilisate in water in a ratio of 1:1000.

Depending on the application, the solubilisate according to the invention may contain up to 5% by weight water and/or between 12% by weight and 20% by weight glycerin.

It has advantageously been found that the solubilisate according to the invention may be easily provided in capsules for oral administration, since it does not attack the capsules. The invention thus also provides a capsule filled with the solubilisate, wherein the capsule may be formed as a soft gelatin capsule or hard gelatin capsule, or as a soft gelatin-free capsule or as a hard gelatin-free capsule.

An additional administration form is a fluid containing the solubilisate according to the invention, wherein the fluid may be a food, a beverage, a cosmetic product such as a cream, lotion, or salve in particular, or a pharmaceutical product. In particular, the fluid may comprise an aqueous dilution of the solubilisate. The usability of the according to the invention in a fluid is not bound to its viscosity; the solubilisate may likewise be incorporated into hydrophilic as well as lipophilic media.

Exemplary embodiments of solubilisates according to the invention are explained below.

The particle size measurements were carried out using a ParticleMetrix NANOTRAC backscattering particle analyzer. The measuring principle is based on dynamic light scattering (DLS) in a 180° heterodyne backscattering system. In this geometry, a portion of the laser beam is mixed with the scattered light. This has the same positive effect with regard to the signal/noise ratio as the superimposition of all light wavelengths in a Fourier spectrometer. The color of the sample has no influence on the quality of the measurement. The measurements were carried out in a 1:1000 aqueous dilution. To this end, the solubilisate was dissolved in water with stirring. The solubilisate is soluble in water, in which it is completely clear. This solution is stable and transparent.

EXAMPLES

Example 1: Curcumin Solubilisate Containing Polysorbate 80

Only 930 g polysorbate 80 and 70 g 95% curcumin powder are used for producing the solubilisate. The 70 g contains 95% curcumin, i.e., 66.5 g of curcumin.

Commercially available preparations such as TEGO SMO 20 V, InCoPa, or Crillet 4/Tween 80-LQ-(SG), Croda, or Lamesorb SMO 80, Cognis are usable as polysorbate 80. Commercially available preparations may likewise be used as 95% curcumin powder, for example Oleoresin Turmeric 95% (curcumin powder), Jupiter Leys, or Curcumin BCM-95-SG, Eurochem, or Curcumin BCM-95-CG, Eurochem, or Curcuma Oleoresin 95%, Henry Lamotte.

The polysorbate 80 is heated to approximately 48° C. to approximately 52° C. The curcumin powder is slowly added to the polysorbate 80, with stirring. During the addition of the curcumin powder, further heating to approximately 87° C. to approximately 91° C. is carried out. The resulting solubilisate is cooled to below approximately 60° C., and is then ready for filling.

The solubilisate is yellow-orange to reddish, very dark, intensely colored, and transparent.

The curcumin portion may be increased to approximately 10% by weight at the expense of the polysorbate 80 portion.

Example 2: Curcumin Solubilisate Containing Polysorbate 20

Only 894 g polysorbate 20 and 106 g 95% curcumin powder are used for producing the solubilisate. The 106 g contains 95% curcumin, i.e., 100.7 g of curcumin.

Commercially available preparations such as TEGO SML 20 V, InCoPa, or Tween 20, Crillet, 1-LQ-(SG), Croda, or Lamesorb SML 20, Cognis are usable as polysorbate 80.

Commercially available preparations may likewise be used as 95% curcumin powder, for example Oleoresin Turmeric 95% (curcumin powder), Jupiter Leys, or Curcumin BCM-95-SG, Eurochem, or Curcumin BCM-95-CG, Eurochem, or Curcuma Oleoresin 95%, Henry Lamotte.

The polysorbate 20 is heated to approximately 63° C. to approximately 67° C. The curcumin powder is slowly added to the polysorbate 20, with stirring. During the addition of the curcumin powder, further heating to approximately 83° C. to approximately 87° C. is carried out. The resulting solubilisate is slowly cooled to below approximately 45° C., and is then ready for filling.

The solubilisate is yellow-orange to reddish, very dark, intensely colored, and transparent.

The curcumin portion may be varied at the expense of the polysorbate 80 portion.

Photographs of samples of various curcumin formulations are shown in appended FIG. 1. The left side of the illustration shows the samples 24 hours after addition to water at a temperature of 21° C., under neutral conditions (pH 7). The right side of the illustration shows the samples under physiological conditions 1 hour after addition to water at a temperature of 37° C., under conditions as in the stomach (pH 1.1). In each case, enough water was added to the starting preparations to give a curcumin concentration of 11.4 g/L in the illustrated sample.

In particular, the following formulations were compared:

Sample A

Curcumin extract, native form, powder, 95% curcumin (BCM 95). 12 g of the powder was introduced into 1 liter of water.

Sample B 17.5% curcumin micronisate, powder, RAPS. 65.1 g of the powder was introduced into 1 liter of water.

Sample C

13% curcumin-formulation, powder, Wacker Chemie. 87.7 g of the powder was introduced into 1 liter of water.

Sample D

Curcumin solubilisate according to the invention according to Example 1. 200 g of the liquid solubilisate was introduced into 1 liter of water.

Sedimentation and phase separation were observed for samples A, B, and C, at room temperature under neutral conditions and also at 37° C. and acidic conditions, whereas sample D was clear and homogeneous. The solubilisate according to the invention also showed no phase separation and no sedimentation over the entire temperature range from −20° C. to 100° C. Furthermore, sample D showed a fairly intense red coloring, at room temperature under neutral conditions and also at 37° C. and acidic conditions, as the result of which the sample appears much darker in a black and white photograph than samples A, B, and C, which have a yellowish-orange color.

It is apparent to one skilled in the art that the invention is not limited to the exemplary embodiments described above, but, rather, may be varied in numerous ways. In particular, the features of the individual exemplary embodiments may also be combined with one another or interchanged with one another.

What is claimed is:

1. A transparent, water-soluble liquid curcumin formulation prepared by a process comprising:
   (a) heating polysorbate 80 to a temperature of about 48° C. to about 52° C.,
   (b) adding curcumin to the polysorbate 80 with stirring and heating the resulting mixture to a temperature of about 87° C. to about 91° C.; and
   (c) cooling the resulting formulation of step (b) to about 60° C.,
   wherein the water-soluble liquid curcumin formulation consists of: curcumin in a quantity of more than 6% by weight to less than or equal to 7.5% by weight; and
   polysorbate 80,
   wherein upon dilution of the transparent, water-soluble liquid curcumin formulation, micelles of curcumin and the polysorbate 80 can be detected,
   wherein the average diameter of the micelles is between 5 nm and 40 nm in a 1:1000 aqueous dilution of the transparent, water-soluble liquid curcumin formulation,
   wherein the width of the diameter distribution of the micelles ranges from approximately 4 nm to approximately 30 nm, and
   wherein the turbidity of a 1:1000 aqueous dilution of the transparent, water-soluble liquid curcumin formulation is less than 20 FNU, determined by scattered light measurement with infrared light according to the requirements of the ISO 7027 standard, measured after 1 hour storage under one or more of the following conditions:
   37° C. and pH 1.1, and
   37° C. and pH 7.

2. A capsule filled with a transparent, water-soluble liquid curcumin formulation according to claim 1, wherein the capsule is formed as a soft gelatin capsule or hard gelatin capsule, or as a soft gelatin-free capsule or as a hard gelatin-free capsule.

3. A fluid containing a transparent, water-soluble liquid curcumin formulation according to claim 1, wherein the fluid is selected from the group consisting of foods, beverages, cosmetics, and pharmaceutical products.

4. The fluid according to claim 3, wherein the fluid comprises an aqueous dilution of the transparent, water-soluble liquid curcumin formulation.

5. The transparent, water-soluble liquid curcumin formulation according to claim 1, wherein the average diameter of the micelles loaded with curcumin is between 6 nm and 20 nm.

6. The transparent, water-soluble liquid curcumin formulation according to claim 1, wherein the average diameter of the micelles loaded with curcumin is between 7 nm and 10 nm.

* * * * *